United States Patent [19]
Blank

[11] Patent Number: 4,533,540
[45] Date of Patent: Aug. 6, 1985

[54] NITROGLYCERIN-CONTAINING POLYMERIC MATRIX FOR SUSTAINED RELEASE ON TOPICAL APPLICATION

[75] Inventor: Izhak Blank, Haifa, Israel

[73] Assignee: Forest Laboratories, Inc., New York, N.Y.

[21] Appl. No.: 646,001

[22] Filed: Aug. 30, 1984

Related U.S. Application Data

[60] Division of Ser. No. 524,369, Aug. 18, 1983, Pat. No. 4,482,534, which is a continuation-in-part of Ser. No. 325,833, Nov. 30, 1981.

[30] Foreign Application Priority Data

Dec. 16, 1980 [IL] Israel ......................... 61721

[51] Int. Cl.³ ...................... A61F 13/00; A61L 15/03; A61K 31/79; A61K 31/21
[52] U.S. Cl. ......................................... 424/28; 424/16; 424/45; 424/80; 514/785; 514/947; 514/970
[58] Field of Search ....................... 424/16, 28, 45, 80, 424/298

[56] References Cited

U.S. PATENT DOCUMENTS

| | | | |
|---|---|---|---|
| 3,725,541 | 4/1973 | Queville et al. | 424/80 |
| 3,972,995 | 8/1976 | Tsuk et al. | 424/28 |
| 3,996,934 | 12/1976 | Zaffaroni | 604/897 |
| 4,091,091 | 5/1978 | Terrill | 424/80 |
| 4,139,688 | 2/1979 | Dixon | 525/326.9 |
| 4,180,633 | 12/1979 | Dixon | 525/326.9 |
| 4,210,633 | 7/1980 | Takruri et al. | 424/28 |
| 4,291,015 | 9/1981 | Keith | 424/28 |
| 4,344,934 | 8/1982 | Martin | 424/80 |
| 4,451,260 | 5/1984 | Mitra | 604/890 |
| 4,482,534 | 11/1984 | Blank | 424/28 |

FOREIGN PATENT DOCUMENTS

| | | | |
|---|---|---|---|
| 1467792 | 12/1968 | Fed. Rep. of Germany | 424/80 |
| 2634004 | 2/1978 | Fed. Rep. of Germany | 424/80 |
| 1090184 | 11/1967 | United Kingdom | 424/80 |
| 1380171 | 1/1975 | United Kingdom | 424/80 |
| 1427881 | 3/1976 | United Kingdom | 424/80 |
| 2021610 | 12/1979 | United Kingdom | 424/80 |

Primary Examiner—Shep K. Rose
Attorney, Agent, or Firm—Jacobs & Jacobs

[57] ABSTRACT

A mixture of nitroglycerin and a water-insoluble vinylpyrrolidone polymer provides a polymeric matrix which gradually releases nitroglycerin upon application to the skin of a patient in the form of a film, gel or ointment. The water-insoluble vinylpyrrolidone polymer may be an uncrosslinked copolymer or a crosslinked homopolymer or copolymer. The polymer provides increased stability and reduced volatility of the nitroglycerin while permitting slow and sustained release of the drug upon topical application to the skin.

12 Claims, No Drawings

NITROGLYCERIN-CONTAINING POLYMERIC MATRIX FOR SUSTAINED RELEASE ON TOPICAL APPLICATION

CROSS-REFERENCE

This is a division of Ser. No. 524,369 filed Aug. 18, 1983, now U.S. Pat. No. 4,482,534, which is a continuation in part of Ser. No. 325,833, filed Nov. 30, 1981.

BACKGROUND OF THE INVENTION

1. Field of Invention

This invention relates to novel compositions of matter for topical application to humans and methods for providing therefrom a predetermined dosage of nitroglycerin. The novel compositions comprise stabilized nitroglycerin in a form adapted for the slow and gradual release thereof so as to provide a sustained level of the drug in the blood of the patient.

2. Description of the Prior Art

Nitroglycerin (glyceryl trinitrate) has been in use for many years as a coronary vasodilator and is especially useful in the treatment of cardiac diseases such as angina pectoris. Nitroglycerin is generally used in the form of sublingual tablets or capsules, composite gradual release tablets, ointments and patches.

Nitroglycerin is rapidly absorbed through mucous membranes and the effect of sublingual tablets starts some 3 minutes after taking the medication and lasts for about 30 minutes. The duration of the effect of tablets taken internally is of the same order of magnitude.

Notwithstanding its efficacy, the high volatility and mobility of the nitroglycerin leads to a loss of the drug to the environment during storage and use. Thus, when tablets containing nitroglycerin and an excipient such as lactose are exposed to the atmosphere in a semienclosed or open container, the loss of nitroglycerin results in a change in the nitroglycerin content of the tablets. Further, the mobility of nitroglycerin is manifested by the migration of the drug from one tablet to another when such tablets are in contact with each other in a closed container over an extended period of time.

The stabilization of nitroglycerin tablets against losses to the atmosphere by volatilization and tablet-to-tablet migration has been accomplished by the incorporation of water-soluble polyvinylpyrrolidone into the mixture of components used in the preparation of the tablets. Thus, Fung et al. in Journal of Pharmaceutical Sciences, 63, 1810 (1974), disclosed that the addition of polyvinylpyrrolidone to a tablet containing nitroglycerin and lactose, retarded the rate of evaporation of the nitroglycerin from the tablet. However, the solid phase stabilization did not affect the availability of the nitroglycerin in an aqueous environment because of the preferential solvation and the rapid solubilization of the vinylpyrrolidone homopolymer in water.

German DOS 2,301,664 and British Pat. No. 1,427,881 disclose the prolongation of the storage stability of nitroglycerin by the addition of polyvinylpyrrolidone. U.S. Pat. No. 4,091,091 describes the stabilization of nitroglycerin against tablet-to-tablet migration by the incorporation of water-soluble polyvinylpyrrolidone in the mixture of a water-soluble excipient and nitroglycerin, while retaining the rapid solubility of the tablet in the mouth.

The release of nitroglycerin as a result of the water-solubility of vinylpyrrolidone homopolymer or copolymers has also been utilized in an antianginal film or plate. Thus, British Patent Application 2 021610 A discloses that a thin film containing nitroglycerin, a water-soluble homopolymer or copolymer or acrylamide and/or vinylpyrrolidone and, optionally a dispersed solid fat, is applied to a site in the mouth and releases the medicament at a rate which is dependent upon the rate of solution of the polymer.

Nitroglycerin is rapidly absorbed through unbroken skin as well as through mucous membranes in the mouth. U.S. Pat. No. 3,742,951 discloses a medical bandage or patch comprising a backing member, a reservoir containing nitroglycerin and a pressure sensitive adhesive coating. The reservoir is in the form of microcapsules or matrix layers which are polymeric, preferably silicone rubbers, and permeable to nitroglycerin. The rate of release of nitroglycerin is controlled by the permeability of the polymer in the microcapsule wall or matrix layer. U.S. Pat. No. 4,336,243 discloses a transdermal delivery system for administration of nitroglycerin wherein the latter is present in microsealed compartments in a polymer which is insoluble in body fluids and through which the nitroglycerin can pass at a controlled rate. The polymer, preferably a silicone rubber, contains a hydrophilic solvent such as polyethylene glycol and a hydrophobic solvent such as mineral oil which partition and enhance the diffusion of nitroglycerin throughout the matrix. U.S. Pat. No. 4,291,015 discloses a water-containing polymeric matrix for the transdermal delivery of nitroglycerin. The matrix contains water and a polar plasticizer such as glycerin, with small amounts of a hydroxyl-containing polymer such as polyvinyl alcohol and a water-soluble polymer such as polyvinylpyrrolidone. The polymers provide retention of the shape of the water-containing matrix.

The absorption of nitroglycerin through unbroken skin makes possible topical application in the form of ointments. Nitroglycerin ointments based on lanolin, vasoline or similar hydrophobic and practically water-insoluble bases are effective for about 3 to 4 hours. However, when these ointments are applied to the skin, part of the nitroglycerin is lost by volatilization and the base is rapidly absorbed into the skin.

The present invention is directed towards improvements in stabilized nitroglycerin compositions which upon topical application will have reduced volatilization of the nitroglycerin, slow release of the drug upon contact with moisture and provide a slow and sustained release of the nitroglycerin so as to maintain the desired sustained level of the drug in the blood of the patient. This is accomplished by the incorporation of water-insoluble vinylpyrrolidone homopolymer or copolymers.

The use of water-soluble polyvinylpyrrolidone in conjunction with medicaments other than nitroglycerin has been disclosed in a number of patents. Thus, U.S. Pat. No. 3,972,995 discloses a buccal dosage form in which the water-soluble homopolymer functions as a binder in an adhesive layer. U.S. Pat. No. 3,214,338 discloses a topical ointment in which the water-soluble homopolymer is added to an emulsifiable polyvinyl acetate powder. U.S. Pat. No. 3,803,300 discloses a film-forming ointment containing water-soluble vinylpyrrolidone homopolymer and copolymers. U.S. Pat. No. 3,287,222 discloses the use of the homopolymer as a water-soluble plasticizer in an impregnating solution for a synthetic fiber medical dressing. U.S. Pat. No. 4,210,633 discloses a water-soluble medicated film containing the water-soluble homopolymer. U.S. Pat. No. 3,608,070 discloses a surgical dressing which is an ointment containing a vinylpyrrolidone copolymer, a thixotropic agent, a water-soluble plasticizer and a solvent such as aqueous ethanol. The film formed on drying the ointment is readily soluble in water. U.S. Pat. No. 2,776,924 discloses the use of water-soluble polyvinylpyrroidone to inhibit adverse reactions from therapeutic agents in topical application.

In these prior art disclosures with medicaments other than nitroglycerin, vinylpyrrolidone polymers are used because of their film-forming ability and/or water solubility. The rapid solubilization of the polymer results in rapid release of the medicament.

The prior art discloses that the use of water-insoluble, crosslinked polyvinylpyrrolidone also promotes the rapid release of medicament. Thus, British Pat. No. 1,380,171 discloses the use of crosslinked, water-insoluble polyvinylpyrrolidone in medicinal tablets containing a drug, to promote rapid disintegration of the tablet in aqueous fluids and increase the availability of the drug. Examples are provided which illustrate that the presence of water-insoluble polyvinylpyrrolidone results in more rapid disintegration and release of the drug as compared with the water-soluble polymer. German Patent Application 2,634,004 discloses the use of crosslinked, insoluble polyvinylpyrrolidone as a carrier material for poorly soluble medicaments in order to accelerate the release thereof when administered orally. German Patent Application 1,467,792 discloses the use of crosslinked polyvinylpyrrolidone as a disintegrating agent to increase the rate of disintegration of a tablet and to promote the extremely rapid release of the drug therein in the digestive tract.

In a non-pharmaceutical application, British Pat. No. 1,090,184 discloses the use of polyvinylpyrrolidone as well as numerous other polymers soluble in nitroglycerin, including polymethyl methacrylate, polyvinyl acetate and non-hardened phenol-formaldehyde resin, as gelatinizing additives in the production of explosive compositions.

SUMMARY OF THE INVENTION

The prior art teaches that water-soluble vinylpyrrolidone homopolymer complexes with nitroglycerin in a solid tablet or film and reduces the volatility and migration of the medicament without reducing the availability of the drug in an aqueous environment. The prior art also teaches that the presence of water-insoluble vinylpyrrolidone homopolymer promotes even more rapid release of a medicament.

Surprisingly, it has now been discovered that the incorporation of water-insoluble vinylpyrrolidone homopolymers or copolymers in an ointment, gel or film containing nitroglycerin provides increased stability and reduced volatility of the nitroglycerin, while permitting slow release of the drug when applied topically to the skin.

It has further been discovered that ointments with sustained release characteristics and reduced volatility of the nitroglycerin can be prepared by the admixture of a dispersion or solution of a water-insoluble vinylpyrrolidone polymer or copolymer with a nitroglycerin solution or triturate and a conventional hydrophobic base such as vasoline, lanolin and the like.

It has further been discovered that films with sustained release characteristics and increased stability of the nitroglycerin can be prepared from a solution containing a water-insoluble vinylpyrrolidone polymer or copolymer and nitroglycerin, wherein the solution is applied per se or after thickening.

DETAILED DESCRIPTION OF THE INVENTION

According to the present invention, it has now been found that important advantages and improvements over prior art compositions containing nitroglycerin and methods of topical application thereof can be obtained by the admixture of a water-insoluble vinylpyrrolidone homopolymer or a water-insoluble vinylpyrrolidone copolymer.

Water-soluble polyvinylpyrrolidone is a commercially available homopolymer and is prepared by the free radical polymerization of the monomer in water or an appropriate solvent. Water-insoluble polyvinylpyrrolidone, suitable for use in the practice of the present invention, may be prepared by heating the water-soluble vinylpyrrolidone homopolymer in air to 150° C. or in the presence of strong alkali at 100° C. or in the presence of a free radical precursor such as ammonium peroxydisulfate at an elevated temperature such as 90° C. or higher. Other methods for insolubilizing the water-soluble homopolymer will be obvious to those skilled in the art.

A water-insoluble copolymer containing at least 95% vinylpyrrolidone may be prepared directly by the polymerization of vinylpyrrolidone in the presence of a polyunsaturated crosslinking monomer such as a dimethacrylate, e.g. ethylene glycol dimethacrylate, triethylene glycol dimethacrylate, trimethylolpropane trimethacrylate and the like, a polyallyl compound such as diethylene glycol bisallyl carbonate, triallyl glycerine, triallyl cyanurate, etc., a polymaleimide such as ethylene bismaleimide, or a polyvinyl compound such as divinylbenzene and the like.

Water-insoluble copolymers of vinylpyrrolidone, which may be used in the practice of this invention, may be prepared by the copolymerization of vinylpyrrolidone with one or more appropriate comonomers in the proportions which yield water-insoluble, uncrosslinked copolymers. Suitable comonomers include acrylic esters, methacrylic esters, vinyl esters, crotonic esters, vinyl ethers, maleic half esters and diesters, vinylene carbonate, styrene, allyl esters, allyl ethers, etc. Other comonomers which are capable of copolymerizing with vinylpyrrolidone and are well known to those skilled in the art may also be used. Toxicological considerations restrict the choice of monomers to those which yield copolymers having a demonstrated lack of toxicological side-effects, on topical application to the skin.

The acrylic, methacrylic, crotonic and maleic esters which may be used in the preparation of the water-insoluble vinylpyrrolidone copolymers which are effective in the practice of the present invention, include the esters of $C_1$–$C_{40}$ linear, branched or cyclic alkanols, aralkanols, phenols and substituted phenols. The copolymers of vinylpyrrolidone and the acrylic, methacrylic, crotonic and maleic esters may be made by copolymerization of vinylpyrrolidone with the appropriate ester or by esterification of copolymers of vinylpyrrolidone and acrylic, methacrylic, crotonic and maleic acids or anhydrides, with the appropriate hydroxyl-containing compound.

The vinyl esters and allyl esters which may be used in the preparation of the water-insoluble vinylpyrrolidone copolymers which are useful in the practice of this invention, include the esters of $C_1$–$C_{40}$ linear, branched or cyclic aliphatic, araliphatic or aromatic carboxylic acids. The copolymers of vinylpyrrolidone and the vinyl esters may be prepared by copolymerization of vinylpyrrolidone with the appropriate vinyl ester or by transesterification of copolymers of vinylpyrrolidone and vinyl acetate or other vinyl esters or by esterification of hydrolyzed copolymers of vinylpyrrolidone and vinyl acetate or other vinyl esters. The copolymers of vinylpyrrolidone and allyl esters may also be prepared either by direct copolymerization or by transesterification or esterification, analogous to the preparation of vinyl ester copolymers with vinylpyrrolidone.

Graft copolymers made by grafting vinyl monomers onto polyvinylpyrrolidone may also be used, e.g. graft copolymers of polyvinylpyrrolidone with acrylic esters, methacrylic esters, styrene, vinyl acetate and the like.

A crosslinking monomer such as previously described may be utilized in the preparation of the copolymers and graft copolymers of vinylpyrrolidone which are useful in the practice of the present invention. Additional comonomers such as unsaturated carboxylic acids including acrylic, methacrylic, crotonic and maleic acids or anhydrides may be incorporated in the copolymers. The uncrosslinked copolymers and graft copolymers of vinylpyrrolidone may be crosslinked in the presence of peroxides or under radiation, by methods well known to those skilled in the art.

The water-insoluble copolymers of vinylpyrrolidone which may be used in the practice of the present invention may be prepared by any of the conventional methods known in the art, including bulk, solution, emulsion, suspension or dispersion polymerization, with appropriate free radical catalysts such as peroxygen compounds, azo compounds, redox systems, radiation and other catalytic techniques for initiating free radical polymerization. Since the method of polymerization is not an integral part of the practice of the present invention, any suitable method known to those skilled in the art may be used.

The amount of one or more comonomers in the water-insoluble vinylpyrrolidone copolymers which are useful in the practice of the present invention, may be varied from 0.1 to 90% by weight. The actual amount is determined by the nature of the comonomer and the concentration necessary to produce a water-insoluble copolymer, either before or after copolymerization.

The stabilized nitroglycerin compositions which are useful in the practice of the present invention and provide sustained release of the medicament, may be prepared by dissolving or dispersing the water-insoluble vinylpyrrolidone homopolymer or copolymer in a solvent such as isopropanol, ethanol or an alcohol-water mixture, and admixing the polymer solution or dispersion with a nitroglycerin solution in ethanol or a nitroglycerin trituration comprised of nitroglycerin and one or more excipients selected from the group consisting of lactose, beta-lactose, milk sugar, fructose, maltose, sucrose, mannitol, sorbitol and the like.

The solution of uncrosslinked water-insoluble vinylpyrrolidone copolymer and nitroglycerin, in the absence or presence of an excipient, may be cast on a suitable surface and the solvent evaporated under ambient pressure or in vacuo, at ambient or slightly elevated temperature. The resultant film on the substrate surface or after removal from the substrate, contains stabilized nitroglycerin and may be cut into strips or tapes which can be taped to the skin of a patient for sustained release of the medicament.

The solution of uncrosslinked, water-insoluble vinylpyrrolidone copolymer and nitroglycerin may be applied directly to the skin of the patient and permitted to evaporate to form a film thereon, containing stabilized nitroglycerin. The latter is slowly released from the film and absorbed into the skin of the patient.

The solution of vinylpyrrolidone polymer and nitroglycerin may be conveniently applied to the skin using an aerosol formulation containing one or more low boiling propellants. Although fluorocarbon propellants such as trichloromonofluoromethane (Propellant 11), dichlorodifluoromethane (Propellant 12) and dichlorotetrafluoroethane (Propellant 114) are particularly effective, other propellants well known to those skilled in the art may be used. The solution of nitroglycerin and water-insoluble vinylpyrrolidone copolymer in ethanol may be pressurized in an aerosol can with a propellant. In order to control the amount of polymer and nitroglycerin applied to the skin, it is advantageous to use a metering valve which delivers precise quantities of solution. When applied in this manner, the propellant and solvent quickly evaporate leaving a dry film of controlled nitroglycerin content covering the desired area of skin.

A gel or thickened solution of nitroglycerin and water-insoluble vinylpyrrolidone copolymer may be applied with greater control to a restricted area of skin than a low viscosity solution. The solution may be thickened by the addition of a small amount of a soluble high molecular weight inert polymer or a thickener of the type well known to those skilled in the art. High surface area inorganic materials such as finely divided fumed silica are particularly effective thickeners. The addition of a small amount of such a material results in a marked increase in the viscosity of the solution. The resultant gel or thickened solution exhibits thixotropy and flows readily during application but does not spread after application to the skin. The large surface area of the thickener increases the rate of evaporation of the solvent and contributes to rapid drying and film formation. The complexed nitroglycerin is slowly released and absorbed into the skin of the patient. At the end of the desired treatment period, or sooner if undesirable reaction to the nitroglycerin is noted, the film may be removed by rubbing with soap and water or alcohol.

A solution or dispersion of uncrosslinked, water-insoluble vinylpyrrolidone copolymer and nitroglycerin, or a dispersion of crosslinked vinylpyrrolidone homopolymer or copolymer and nitroglycerin, in the absence or presence of an excipient, may be applied to a porous or open-structured substrate such as gauze, bandage tissue or paper, and upon evaporation of the solvent, provides an impregnated structure containing stabilized nitroglycerin, which is released over an extended period of time when applied topically to the skin of a patient.

The solution or dispersion of water-insoluble vinylpyrrolidone homopolymer or copolymer and nitroglycerin may be mixed, with stirring, with one or more ointment bases, such as petrolatum, vasoline, lanolin, stearin, spermaceti wax or other waxy or fatty material. The ointment may be applied directly to the skin of a patient or may be coated on a carrier such as a bandage or polymeric tape for topical application to the skin of a patient. The stabilized nitroglycerin is slowly released and absorbed into the skin of the patient for as long as 24 hours.

The nitroglycerin in the vinylpyrrolidone homopolymer or copolymer-nitroglycerin composition used in the practice of the present invention, is slowly released and absorbed directly into the skin of the patient. However, although the vinylpyrrolidone homopolymer or copolymer is water-insoluble, the hydrophilicity of the vinylpyrrolidone contained therein results in moisture absorption, e.g. from perspiration on the skin of the patient, and extraction of the nitroglycerin from the composition, followed by absorption of the drug into the skin. The rate of extraction may be varied over a wide range and is dependent upon the concentration of vinylpyrrolidone in the copolymer and/or the extent of crosslinking, if any, in the homopolymer or copolymer.

The concentrations of water-insoluble vinylpyrrolidone homopolymer or copolymer and nitroglycerin in the stabilized compositions of the present invention, may be varied over a wide range, depending upon the desired release rate. The nitroglycerin concentration may range from about 1 to about 6% of the total weight of the composition, while the concentration of water-insoluble vinylpyrrolidone homopolymer or copolymer may range from about 5 to about 500% of the weight of the nitroglycerin.

The following examples are non-limiting illustrative embodiments of the compositions and methods of the present invention. Variations thereof will be obvious to those skilled in the art.

EXAMPLE I

An uncrosslinked vinylpyrrolidone (VP) homopolymer, a crosslinked 98/2 weight ratio vinylpyrrolidone/ethylene glycol dimethacrylate (VP/EGDM) copolymer, an uncrosslinked 70/30 weight ratio vinylpyrrolidone/lauryl methacrylate (VP/LM) copolymer and an uncrosslinked 79/21 weight ratio vinylpyrrolidone/vinyl acetate (VP/VA) copolymer were prepared by solution polymerization in cyclohexane using lauroyl peroxide as catalyst. The viscous reaction mixture was cast on a polytetrafluoroethylene sheet and the solvent was permitted to evaporate. The resultant thin film was dried at 60° C. in a forced air oven, washed free of residual monomer, if any, with petroleum ether and redried in vacuo at 60° C.

Ointments were prepared by dissolving or suspending the various polymers in ethanol. An ethanol solution containing 10 w/v % nitroglycerin (NG) or a nitroglycerin-lactose powder containing 10 weight-% nitroglycerin was added slowly to the polymer solution or suspension with stirring. Vasoline was slowly added to the homogeneous polymer-nitroglycerin mixture with stirring. The final ointment composition contained 20% polymer and 4% nitroglycerin. A polymer-free ointment containing 4% nitroglycerin was prepared for comparison.

In order to determine the stability of the nitroglycerin to evaporation under drastic conditions, samples of the ointments were placed on 10×10 cm squares of filter paper. The coated paper was hung for several days until the ethanol evaporated. Samples containing 4% nitroglycerin were placed in a forced air oven at 45° C. and removed after 4.5 to 17 days and analyzed for nitroglycerin content.

In order to determine the rate of release of the nitroglycerin to an aqueous medium, samples of the coated filter paper containing dried ointments with 4% nitroglycerin were folded to make an envelope and placed in 250 ml Erlenmeyer flasks containing 100 ml deionized water. The flasks were placed in a 36° C. thermostatted shaker bath and samples of the liquid phase were removed for nitroglycerin analysis after shaking for 15, 30 and/or 60 minutes.

The nitroglycerin analyses were carried out by a modification of the spectrophotometric method described by Fung et al. (J. Pharm. Sci., 63, 1810 (1974).

The stability of the nitroglycerin to evaporation, as indicated by the results of the thermal aging at 45° C., and the rate of release of the nitroglycerin in water at 36° C., are summarized in Table I.

The results in Table I indicate that the polymer-free control ointment lost all of the nitroglycerin after 4.5 days in the oven at 45° C. while releasing 48 and 57% of the nitroglycerin in water at 36° C. after 15 and 30 minutes, respectively. The ointment containing the water-soluble uncrosslinked polyvinylpyrrolidone still retained 93% of the nitroglycerin after 17 days in the oven while releasing all of the nitroglycerin after 30 minutes in water. The ointment containing water-insoluble crosslinked 98/2 VP/EGDM copolymer retained 76% of the nitroglycerin after 17 days in the oven and released 45 and 65% of the nitroglycerin after 15 and 60 minutes, respectively, in water.

TABLE I

| Polymer | none | VP | VP/EGDM 98/2 | VP/LM 70/30 | VP/LM 70/30 | VP/VA 79/21 |
|---|---|---|---|---|---|---|
| Ointment | | | | | | |
| Polymer, % | 0 | 20 | 20 | 20 | 20 | 20 |
| NG, % | 4 | 4 | 4 | 4 | 4* | 4 |
| Thermal aging at 45° C. | | | | | | |
| Residual NG, % of original | | | | | | |
| after 0 days | 100 | 100 | 100 | 100 | 100 | 100 |
| 4.5 days | 0 | 100 | | | | 100 |
| 7 days | | | 77 | 42 | 49 | |
| 8 days | | | | | | 83 |
| 17 days | | 93 | 76 | 13 | 20 | 77 |
| Extraction by water at 36° C. | | | | | | |
| Extracted NG, % of original | | | | | | |
| after 15 minutes | 48 | 82 | 45 | 0 | 0 | 58 |
| 30 minutes | 57 | 100 | | 28 | 7 | |
| 60 minutes | | | 65 | 31 | 29 | 71 |

*NG added as 10% NG in lactose

The ointment containing the 70/30 VP/LM water-insoluble uncrosslinked copolymer was less stable to thermal aging than the crosslinked VP/EGDM ointment but released about 30% of the nitroglycerin after 60 minutes in water. The ointment containing the uncrosslinked water-insoluble 79/21 VP/VA copolymer behaved in a manner similar to the ointment containing the crosslinked polyvinylpyrrolidone, retaining 77% of the nitroglycerin after 17 days in the oven and releasing 58 and 71% of the nitroglycerin after 15 and 60 minutes, respectively, in water.

EXAMPLE II

A 64/36 vinylpyrrolidone/2-ethylhexyl acrylate weight ratio copolymer was prepared in isopropanol solution using lauroyl peroxide as catalyst. After 4.5 g of the 60% solution of the VP/EHA copolymer in isopropanol was mixed with 12 ml of a 10% w/v solution of glyceryl trinitrate in ethanol, 42 g of white petrolatum was mixed in to give an ointment containing 2% nitroglycerin.

Nine patients suffering from coronary artery disease and angina pectoris were used in a clinical trial. A 5–10 cm long extrudate was dispensed from a metal tube containing the ointment onto the forearm of each patient, covered with an impermeable pad and taped in place. The effectiveness of the ointment was tested by radioisotopic techniques, using multigated equilibrium blood volumes.

The first 5 patients were tested 5 hours after the application of the ointment. There was a significant improvement in left ventricular ejection fraction, diastolic volume decreased significantly at rest and systolic volumes decreased significantly at rest and during exercise. All 9 patients were tested 24 hours after the application of the ointment. Ejection fractions improved both at rest and during exercise and diastolic and systolic volumes decreased at rest and during exercise. Thus, the application of the ointment containing 2% nitroglycerin and the VP/EHA copolymer had beneficial effects on the cardiovascular system as early as 5 hours after application and the effects persisted for at least 24 hours.

EXAMPLE III

A 62.5/32.5/5 weight ratio vinylpyrrolidone/lauryl methacrylate/acrylic acid copolymer was prepared by polymerization in cyclohexane using lauroyl peroxide as catalyst. The polymer was isolated in the same manner as described in Example I. The polymer was dissolved in ethanol and blended with a 10% w/v solution of nitroglycerin in ethanol, to yield a solution containing 15% VP/LM/AA copolymer and 3% nitroglycerin. The solution was cast on a cotten tape and dried in air. The tape was applied to the forearm of a patient with angina pectoris and relieved the symptoms for more than 24 hours.

EXAMPLE IV

A 42.5/52.5/5 weight ratio vinylpyrrolidone/lauryl methacrylate/acrylic acid copolymer was prepared in the same manner as described in Example III. An ethanolic solution containing 10% VP/LM/AA copolymer and 3% nitroglycerin was mixed with lanolin to produce an ointment which was used to impregnate gauze and dried. The impregnated gauze was covered with a silicone-coated release paper and packed in a multilayer, heat-sealed pouch containing an aluminum foil layer. When needed, the impregnated gauze was removed from the storage pouch and taped to the arm of a patient with the symptoms of angina pectoris. The symptoms were relieved in about 2 hours and the relief persisted for 24 hours.

EXAMPLE V

A 90/10 weight ratio vinylpyrrolidone/lauryl methacrylate copolymer as well as a 10/90 weight ratio copolymer was prepared by solution polymerization in cyclohexane using lauroyl peroxide as catalyst.

The isolated 90/10 VP/LM copolymer was a brittle solid which was mixed with nitroglycerin-lactose powder in ethanol solution and the resultant solution containing 3% nitroglycerin was used to impregnate a gauze bandage. The dried impregnated bandage relieved the symptoms of angina pectoris within 1 hour after application to the arm of a patient.

The isolated 10/90 VP/LM copolymer was a viscous semisolid which was converted into an ointment containing 10% VP/LM copolymer and 4% nitroglycerin. When applied to the arm of a patient and covered with an impermeable polymer film such as polyethylene, the ointment relieved the symptoms of angina pectoris for 24 hours.

EXAMPLE VI

A 70/30 weight ratio vinylpyrrolidone/lauryl methacrylate copolymer was prepared by solution polymerization in isopropanol using lauroyl peroxide as catalyst. The polymer was isolated as described in Example I. The polymer was dissolved in ethanol and blended with a 10% w/v solution of nitroglycerin in ethanol to yield a solution containing 16% VP/LM copolymer and 4% nitroglycerin. The solution was placed in an aerosol can fitted with a metering valve and pressurized with Propellants 11 and 12. A film was prepared by spraying the solution on a 10×10 cm square of filter paper. The film was formed very rapidly due to the evaporation of the volatile propellants and solvent. The sample was placed in an oven at 45° C. for 72 hours. Analysis indicated that the sample retained 68% of the original amount of nitroglycerin.

EXAMPLE VII

The 70/30 weight ratio VP/LM copolymer prepared in Example VI was dissolved in ethanol and mixed with a 10% w/v solution of nitroglycerin in ethanol, as described in Example VI. A small amount of Aerosil 200 fumed silica was added in portions until a gel having a viscosity of about 10,000 cps was obtained. The gel was applied to a strip of filter paper and formed a flexible, nontacky film in 2 minutes. After 72 hours in an oven at 45° C., the film retained 71% of the original amount of nitroglycerin.

Although the description and examples given hereinbefore have been limited to nitroglycerin, it should be understood that the present invention is applicable to the other organic nitrate esters known to those skilled in the art as coronary vasodilators, e.g. isosorbide dinitrate, erythrityl tetranitrate, etc.

What is claimed is:

1. A composition for the sustained transdermal administration of nitroglycerin, comprising a film or solution containing a mixture of nitroglycerin and an uncrosslinked water-insoluble vinylpyrrolidone copolymer containing at least 10% by weight vinylpyrrolidone, wherein the nitroglycerin concentration is within the range of about 1% to about 6% of the total weight of the composition.

2. A composition for the sustained transdermal administration of nitroglycerin, comprising a film or solution containing a mixture of nitroglycerin and an uncrosslinked water-insoluble vinylpyrrolidone copolymer containing at least 10% by weight vinylpyrrolidone and units derived from an ester of an unsaturated acid selected from the group consisting of acrylic acid, methacrylic acid, crotonic acid, maleic acid and the corresponding anhydrides, wherein the nitroglycerin concentration is within the range of about 1% to about 6% of the total weight of the composition.

3. The composition of claim 2, wherein the ester is selected from the group consisting of the acrylic and methacrylic esters of $C_4$–$C_{18}$ linear and branched alkanols.

4. The composition of claim 3, wherein the ester is lauryl methacrylate.

5. The composition of claim 3, wherein the ester is 2-ethylhexyl acrylate.

6. A composition for the sustained transdermal administration of nitroglycerin, comprising a film or solution containing a mixture of nitroglycerin and an uncrosslinked, water-insoluble vinylpyrrolidone copolymer containing at least 10% by weight vinylpyrrolidone and units derived from an ester of a saturated acid selected from the group consisting of the vinyl and allyl esters of $C_1$–$C_{40}$ carboxylic acids, wherein the nitroglycerin concentration is about 1% to about 6% of the total weight of the composition.

7. The composition of claim 6, wherein the ester is vinyl acetate.

8. A composition for the sustained transdermal administration of nitroglycerin, comprising a film or solution containing a mixture of nitroglycerin and an uncrosslinked water-insoluble copolymer of vinylpyrrolidone and styrene containing at least 10% by weight vinylpyrrolidone, wherein the nitroglycerin concentration is within the range of about 1% to about 6% of the total weight of the composition.

9. The composition of claim 2, wherein the uncrosslinked water-insoluble vinylpyrrolidone copolymer contains units derived from an unsaturated acid selected from the group consisting of acrylic acid, methacrylic acid, crotonic acid, maleic acid and the corresponding anhydrides.

10. The composition of claim 6, wherein the uncrosslinked water-insoluble vinylpyrrolidone copolymer contains units derived from an unsaturated acid selected from the group consisting of acrylic acid, methacrylic acid, crotonic acid, maleic acid and the corresponding anhydrides.

11. A method for providing for the sustained transdermal administration of nitroglycerin, which comprises applying to the skin of a patient a film or solution containing nitroglycerin and an uncrosslinked, water-insoluble vinylpyrrolidone copolymer which contains at least 10% by weight of vinylpyrrolidone, wherein the nitroglycerin concentration is in the range of about 1% to about 6% of the total weight of the composition.

12. The method of claim 11, wherein the solution is applied from an aerosol formulation.

* * * * *